United States Patent [19]

Boone

[11] Patent Number: 4,874,387

[45] Date of Patent: Oct. 17, 1989

[54] COVER FOR BODY FLUID DRAINAGE BAG AND TUBING

[76] Inventor: Delores A. Boone, 1092 Kennedy St., Norfolk, Va. 23513

[21] Appl. No.: 265,440

[22] Filed: Nov. 1, 1988

[51] Int. Cl.⁴ ............................................. A61M 1/00
[52] U.S. Cl. ................................................... 604/326
[58] Field of Search ............... 604/317, 326, 332–345, 604/263, 322, 323; 150/154

[56] References Cited

U.S. PATENT DOCUMENTS

| | | | |
|---|---|---|---|
| 2,800,905 | 7/1957 | Simmons et al. | 128/227 |
| 2,856,932 | 10/1958 | Griffitts | 128/294 |
| 3,444,860 | 5/1969 | Harrell | 128/349 |
| 3,547,123 | 12/1970 | Sachs | 128/295 |
| 4,122,851 | 10/1978 | Grossner | 128/295 |
| 4,511,358 | 4/1985 | Johnson, Jr. et al. | 604/327 |
| 4,533,355 | 8/1985 | Fair | 604/343 |
| 4,772,275 | 9/1988 | Erlich | 604/263 |

Primary Examiner—Jerome Kruter
Attorney, Agent, or Firm—Griffin, Branigan & Butler

[57] ABSTRACT

A cover for a body fluid drainage bag (10) and the tubing (12) thereof comprises an envelope shaped bag cover (14) and a tubing cover (16). The tube cover comprises an elongated sheet of flexible material having first and second mating tube-forming attachment devices (78 and 82) at opposite side edges thereof so that the side edges (76 and 8) can be held together to form a tubular shape about the tubing of a body fluid drainage bag. The tubing cover is separate from the envelope shaped bag cover, however, it is attachable to the envelope shaped bag cover and can extend down into any one of a plurality of openings (54, 56, and 58) into the envelope-shaped bag cover. Two spaced closing flaps (48 and 50) are at an open edge (59) of the envelope-shaped bag cover. The envelope-shaped bag cover has a viewing window (34) therein so that one can see accumulated body fluids in the body fluid drainage bag therein.

8 Claims, 2 Drawing Sheets

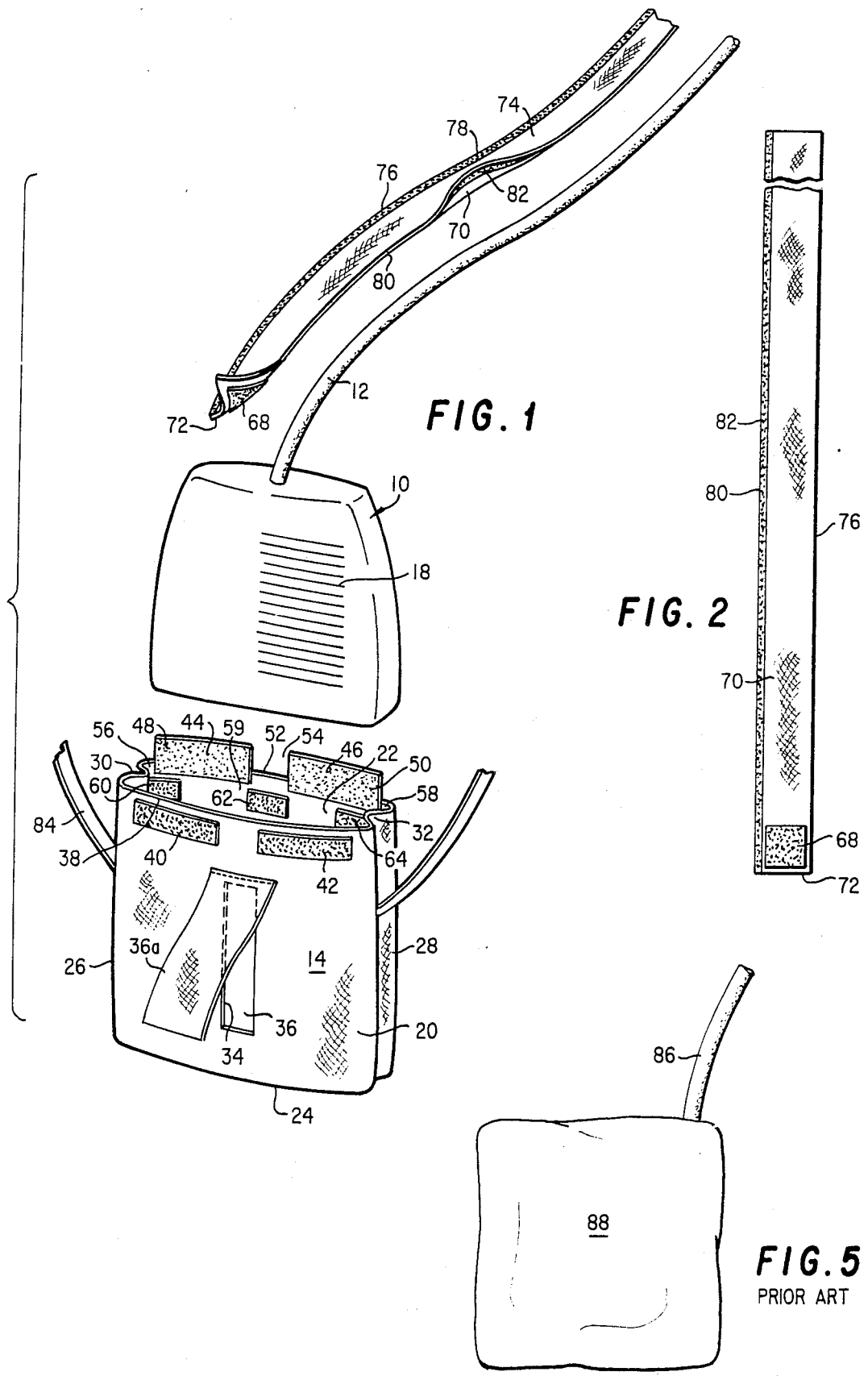

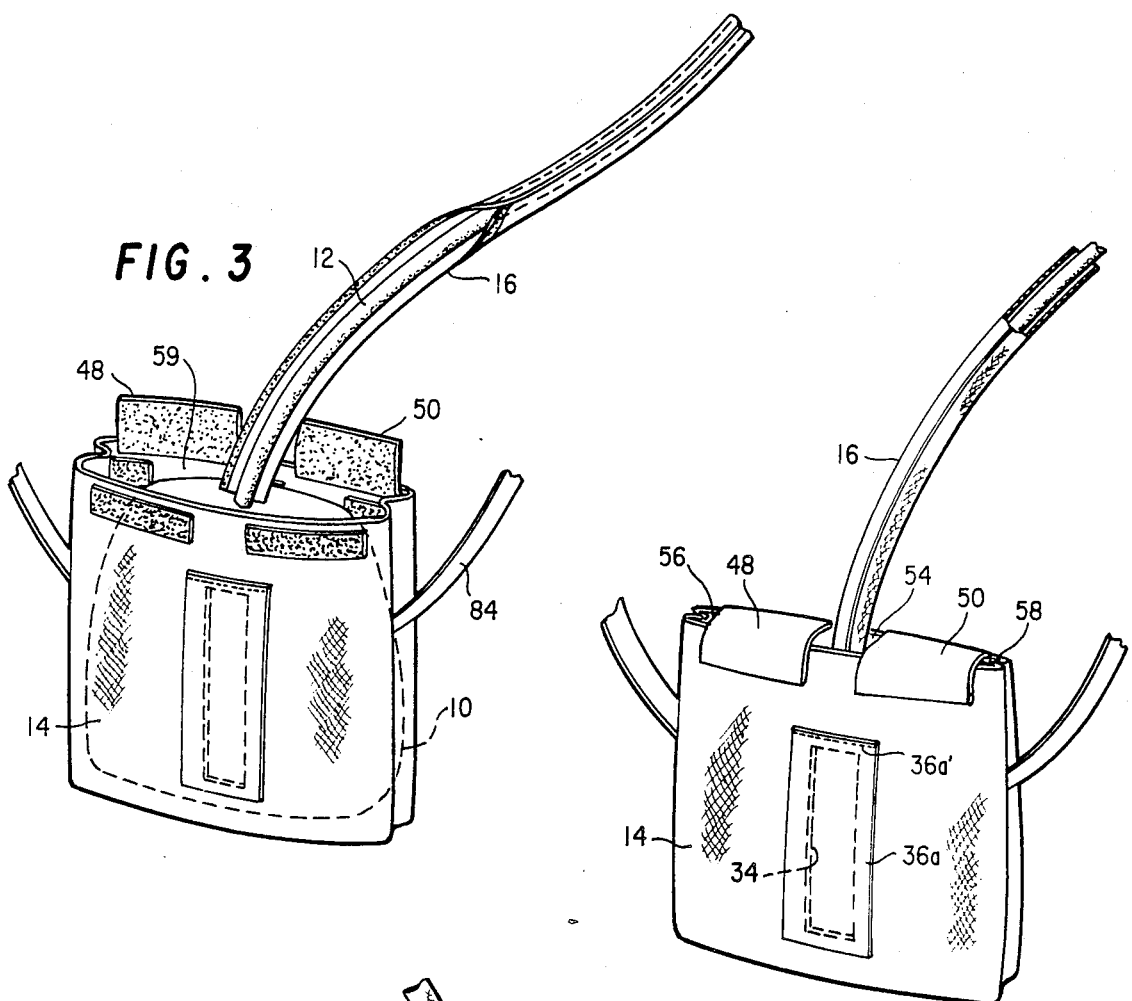
FIG. 3
FIG. 4
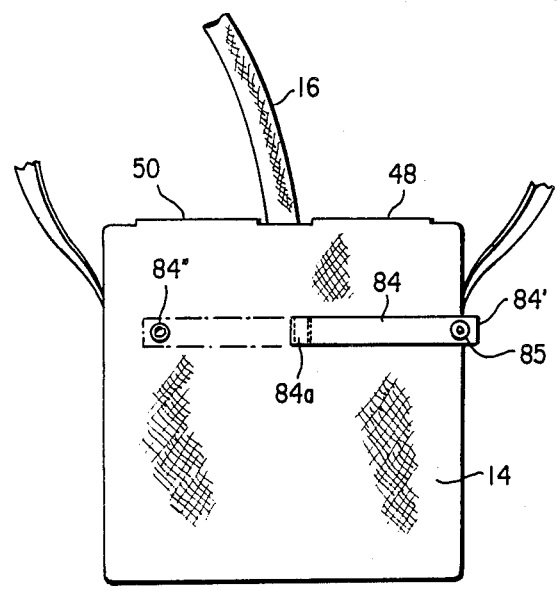
FIG. 4A ary difficulty with prior-art body-fluid drainage bag covering devices is that they are difficult to mount on bodies. In this regard, when they are worn under clothing, they must either be attached to the clothing or to persons' bodies. If they are attached to clothing, the clothing might be damaged and will probably be pulled in undesirable manners by the weights of the bags. If they are attached to the bodies, the attachment devices must be easy to remove in combination with the clothes in order to empty the body-fluid drainage bags. It is an object of this invention to provide a cover for a body-fluid drainage bag and related tubing which can be easily attached to a person's body without damaging his or her clothes and which allows easy access to the body-fluid drainage bag.

COVER FOR BODY FLUID DRAINAGE BAG AND TUBING

BACKGROUND OF THE INVENTION

This invention relates broadly to the art of body fluid drainage bags and tubing therefore, and more specifically to covers for these items.

There are numerous persons who for various reasons have permanent or temporary tubular catheters extending into their bodies in order to drain body fluid to outside their bodies. For example, so called supra-pubic catheters extend into patient's bladders via incisions in abdominal cavities rather than via urinary tracts. Many of these patients are otherwise quite healthy and often are completely ambulatory. Thus, body-mounted or support-mounted drainage bags are frequently attached to outside ends of such tubular catheters for collecting body fluids, such as urine, flowing out of bodies through these tubular catheters.

People who must use such body-fluid drainage bags are often exposed to the viewing public and, as can be imagined, are somewhat self conscious about others seeing unsightly drainage bags and tubing attached to them. Thus, it is an object of this invention to allow a patient to use a body-fluid drainage bag and the related tubing without the elements being visible to others.

Most patients using body-fluid drainage bags and tubing have worn these items under their normal clothes so as to shield them from the view of others, however, keeping these items under clothes can be inconvenient and is often impractical. In this respect, one must normally have easy access to a drainage bag so that he or she can periodically check the amount of fluid drained into the bag and so that he or she can empty the drainage bag at the appropriate time. Drainage bags worn under clothes are difficult to check without removing, or pulling back, in an undignified manner, portions of the clothing. At the same time, it is also quite difficult to empty such drainage bags worn under the clothing because access through the clothing must first be gained thereto. Thus, it is an object of this invention to provide covering for a body-fluid drainage bag and tubing which allows easy access thereto and inspection thereof.

Yet another difficulty with prior-art body-fluid drainage bag covering devices is that they are difficult to mount on bodies. In this regard, when they are worn under clothing, they must either be attached to the clothing or to persons' bodies. If they are attached to clothing, the clothing might be damaged and will probably be pulled in undesirable manners by the weights of the bags. If they are attached to the bodies, the attachment devices must be easy to remove in combination with the clothes in order to empty the body-fluid drainage bags. It is an object of this invention to provide a cover for a body-fluid drainage bag and related tubing which can be easily attached to a person's body without damaging his or her clothes and which allows easy access to the body-fluid drainage bag.

SUMMARY

A cover for a body-fluid drainage bag and tubing comprises an envelope-shaped bag cover and a separate tubing cover of an elongated sheet of flexible material with first and second tube-forming attachment devices mounted at side edges thereof. The sheet of flexible material can be wrapped about body-fluid drainage tubing with the first and second tube-forming attachment means holding the sheet in a tubular shape. The tube cover has an end-edge attachment device which engages the bag cover at any one of various tube openings into the bag cover. Thus, a body-fluid drainage bag can be placed in the envelop-shaped bag cover with its tubing and tube cover extending through one of the tube openings. The bag cover has a window therein to allow a user to check drainage into the drainage bag. There are two, spaced, closing flaps for the bag cover to provide a central opening and two side tube openings.

BRIEF DESCRIPTION OF THE DRAWING

The foregoing and other objects, features and advantages of the invention will be apparent from the following more particular description of a preferred embodiment of the invention, as illustrated in the accompanying drawings in which reference characters refer to the same parts throughout the different views. The drawings are not necessarily to scale, emphasis instead being placed upon illustrating principles of the invention in a clear manner.

FIG. 1 is an isometric, exploded, view of a cover for a body-fluid drainage bag and tubing of this invention along with a drainage bag and tubing;

FIG. 2 is a plan view of an outside surface of a tubing cover portion of the cover of FIG. 1;

FIG. 3 is an isometric view of the same structure of FIG. 1, however, with the body-fluid drainage bag in its cover and the tubing cover portion only partially enclosing tubing of the drainage bag;

FIG. 4 is a view similar to FIG. 3, but with closing flaps of the cover for the body-fluid drainage bag being closed and the tubing cover enclosing tubing of the drainage bag;

FIG. 4A is a back isometric view of the items shown in FIG. 4; and

FIG. 5 is a side view of another prior-art body-fluid drainage bag and tubing therefor in which the tubing is off center.

DESCRIPTION OF THE PREFERRED EMBODIMENT

Referring now to the drawings, a cover for a body-fluid drainage bag 10 and its tubing 12 comprises an envelope-shaped bag cover 14 and a tubing cover 16. The drainage bag 10 and tubing 12 are normally constructed of a transparent plastic so that one can check the drainage of fluids through the tubing 12 and into the drainage bag 10. In this regard, quite often, such drainage bags will have graduated indicia 18 thereon so that one can read an approximate volume from the drainage bag 10 to estimate the volume of body fluids therein.

The bag cover 14 is constructed of a cloth material, such as cotton, cotton blends, muslin, or the like to be flexible, but yet to also be easily washable. The drainage-bag cover 14 is rather flat having front and back panels 20 and 22 joined at a bottom edge 24 and side edges 26 and 28 by edge panels. Side edge panels 30 and 32 are pleated to allow the front and back panels 20 and 22 to be moved toward and away from one another thereby accommodating various depth dimensions of drainage bags 10. In one embodiment the front and back panels 20 and 22 are rather rigid.

The front panel 20 has a window 34 therein which is covered by a transparent flexible plastic 36. A nontransparent, opaque, washable cloth, cover flap 36a is sewn to the bag cover 14 at 36a' above the window 34 for covering the window 34 unless lifted by a user for observing the window 34. Mounted on an outside surface, near a top edge 38, of the front panel 20 are strips of hook portions 40 and 42 of hook and loop fastener pairs (such as sold under the registered trademark VELCRO). The loop portions 44 and 46 of these hook and loop fastener pairs are mounted on inside surfaces of closing flaps 48 and 50 which are attached at an upper edge 52 of the back panel 22. The two closing flaps 48 and 50 are spaced from one another to form a central tube opening 54 therebetween and are slightly spaced from the side panels 30 and 32 to form side tube openings 56 and 58. These openings can perhaps be seen best in FIG. 4 where the closing flaps 48 and 50 are shown closed so as to define the central opening 54 and the to side openings 56 and 58. In this closed position, the loop portions 44 and 46 of the fastener pairs on the closing flaps 48 and 50 are engaged with the hook portions 40 and 42 of the fastener pairs. The top edges 38 and 52 of the front and back panels 20 and 22 are otherwise separate from one another to form a cover mouth, or open edge 59.

Also, found on the bag cover 14 are fastener hook portions 60, 62, and 64 mounted on an inside surface 66 of the back panel 22, one being located at each of the central tube opening 54 and side openings 56 and 58. These fastener hook portions 60, 62 and 64 are for selectively mating with a complementary fastener loop portion 68 mounted on an outside surface 70 of the tubing cover 16 at a first end 72 thereof. The tubing cover 16 comprises mainly an elongated sheet of flexible cloth material, such as cotton, cotton blends, muslin, and the like having an inside surface 74 and the outside surface 70. The tubing cover 16 must also be easily washable. Mounted along a first side edge 76 of the sheet of material is a fastener hook portion 78 on the inside surface 74 and mounted along a second side edge 80 on the outside surface is the mating fastener loop portion 82. The fastener hook portion 78 and the fastener loop portion 82 form an attachment system such that when these two members are engaged together they hold the tubing cover 16 in a tubular shape. Thus, the tubular cover 16 can be wrapped about the tubing 12 and held in this position by the hook and loop fastener portions 78 and 82, as is shown in FIGS. 3 and 4.

A washable cloth strap 84 is sewn to the rear of the bag cover 14 at 84a for hanging the bag cover 14 below the waist of a patient in order to provide proper drainage therefrom. A male metallic, "snap" fastener 84' near an outer end 85 of the strap 84 can be fastened to a female fastener 84" on the bag cover 14 to form a loop, shown in dashed lines, for attaching the bag cover 14 to objects such as wheelchair supports and the like.

In operation of the cover of this invention, a drainage bag 10, which is attached to a tubing 12 extending from a patient's body, is inserted into the cover mouth 59 of the bag cover 14 and the tubing extends out through the open mouth 59. The tubing cover 16 is then folded about its longitudinal axis so as to form a loop about the body fluid tubing 12 with the first end 72 thereof being near the drainage bag 10. The hook and loop fastener portions 78 and 82 are engaged with one another so as to hold the tubing cover 16 about the drainage tubing 12. The loop fastener portion 68 on the outside surface of the tubing cover 16 is then engaged with the hook fastener portion 62 on the inside surface of the back panel 22 at the central opening 54. The closing flaps 48 and 50 are then folded downwardly onto the hook fastening portions 40 and 42 on the front panel 20 so that the loop portions 44 and 46 of the closing flaps 48 and 50 engage the hook fastener portions 40 and 42 on the front panel 20 to close the mouth 59 of the bag cover 14 but leaving the fluid-drainage tubing 12, with its covering tubing cover 16, extending out through the central opening 54. The strap 84 is attached to a wheelchair support or the like to support the bag cover 14, and its contained drainage bag 10.

In the preferred embodiment, the bag cover 14 and the tubing cover 16 have the same color patterns so that they appear to go together, and the colors are quite conservative so that they will go with most clothing.

The user can periodically check drainage into the drainage bag 10 through the window 34 by simply lifting the cover flap 36a. Should it be necessary to empty the drainage bag 10, this can be easily accomplished by lifting the closing flaps 48 and 50, removing the drainage bag 10, emptying it, and again inserting it into the bag cover 14.

It will be appreciated by those of ordinary skill in the art that the bag cover 14 and the tubing cover 16 somewhat resemble a hand bag and strap and are therefore not displeasing in appearance. Further, the cover of this invention is extremely practical, allowing patients to easily check and empty their drainage bags. Further, the cover of this invention can be used with different types of drainage bags 10. Some drainage bags do not have centrally positioned tubing such as tubing 12 shown in FIG. 1, but rather tubing 86 which is off center to a drainage bag 88 (see FIG. 5). When this is the case, the tubing 12 and the tubing cover 16 extend through one of the side openings 56 or 58 rather then through the central opening 54 as is shown in FIG. 4. By having a central and two side openings 54, 56, and 58 the cover of this invention allows the tubing to extend easily toward a patient's back or toward a patient's front while allowing the bag cover to be worn on the patient's side. Also, the tubing cover 16 can be easily opened to check for blockages in the tube 12. In each of these positions the respective fastener hook portion 60, 62 or 64 located at the utilized opening mates with the fastener loop portion 68 on the tubing cover 16.

While the invention has been particularly shown and described with reference to a preferred embodiment, it will be understood by those skilled in the art that various changes in form and detail may be made therein without departing from the spirit and scope of the invention. For example, it may not be necessary to utilize flexible transparent plastic in the window 34. Also, the window 34 could be in the back panel 22 rather than in the front panel 20, thereby possibly making the cover flap 36a unnecessary. Still further, it would be possible to fasten the bag cover 14 to a patient by means other than a strap 84.

The embodiments of the invention in which an exclusive property or privilege are claimed are defined as follows:

1. A cover for a body fluid drainage bag and tubing in combination comprising:
   a bag cover having front and back panels which are joined along end and bottom edges, but which are separated along a top edge to form an open edge, said bag cover being of a size for enclosing a transparent body-fluid bag between the front and back panels;

a tubing cover comprising an elongated sheet of flexible material having first and second opposite side edges and first and second opposite end edges, said tube cover further including a tube forming attachment means for selectively attaching the first and second opposite side edges together so as to hold the sheet of flexible material in a tubular shape or for selectively separating to allow the elongated sheet of flexible material to be opened up with its side edges apart;

an end-edge attachment means for engaging said first end of said elongated sheet of flexible material and said bag cover near the top edge thereof for holding said first end of said elongated sheet in said open edge of said bag cover;

whereby a fluid drainage bag can be placed in said bag cover with said tubing extending through said open edge, said tubing outside said bag cover being covered by said elongated sheet of flexible material held in a tubular shape by said tube forming attachment means about said tubing.

2. A cover as in claim 1 wherein, said tube forming attachment means has first and second tube forming attachment members respectively attached at said first and second opposite side edges of said elongated sheet of flexible material for engaging one another to hold said elongated sheet of flexible material in a tubular shape about said tubing.

3. A cover as in claim 2 wherein, said end edge attachment means has first and second attachment members respectfully mounted to said first end of said sheet of flexible material and to an inside surface of said bag cover.

4. A cover as in claim 1 wherein, said cover further includes at least two closing flaps mounted on said back panel at the top edge thereof for being folded over the open edge of said front panel and engaging said front edge to close said open edge of said bag cover, there being a space between said cover flaps and spaces between ends of said cover flaps and end edges of said outside panels so as to leave at least three openings at said open edge of said bag cover when said cover flaps are folded onto said front panel.

5. A cover as in claim 4 wherein, is further included a window means in at least one of said front and rear panels for allowing a user to look therethrough and observe the amount of body fluids in said drainage bag.

6. A cover as in claim 5 wherein, is further included a cover flap attached to the outer surface of said bag cover for selectively covering and uncovering said window.

7. A cover as in claim 1 wherein, is further included a window means in at least one of said front and rear panels for allowing a user to look therethrough and observe the amount of body fluids in said drainage bag.

8. A cover as in claim 7 wherein, is further included a cover flap attached to the outer surface of said bag cover for selectively covering and uncovering said window.

* * * * *